(12) United States Patent
Juraszyk et al.

(10) Patent No.: US 6,689,885 B2
(45) Date of Patent: Feb. 10, 2004

(54) METHOD FOR PRODUCING THIENOPYRIMIDINES

(75) Inventors: Horst Juraszyk, Seeheim (DE); Peter Wendel, Aschaffenburg (DE); Markus Woissyk, Bensheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/149,125

(22) PCT Filed: Dec. 7, 2000

(86) PCT No.: PCT/EP00/12351
§ 371 (c)(1),
(2), (4) Date: Oct. 21, 2002

(87) PCT Pub. No.: WO01/42248
PCT Pub. Date: Jun. 14, 2001

(65) Prior Publication Data
US 2003/0096994 A1 May 22, 2003

(30) Foreign Application Priority Data
Dec. 7, 1999 (DE) .......................... 199 58 926

(51) Int. Cl.$^7$ ............................................. C07D 495/04
(52) U.S. Cl. ......................................................... 544/250
(58) Field of Search ......................................... 544/250

(56) References Cited

PUBLICATIONS

K.G. Dave et al., "Reaction of Nitriles Under Acidic Conditons. Part I. A General Method of Synthesis of Condensed Pyrimidines," Journal of Heterocyclic Chemistry, vol. 17, 1980, pp. 1497–1500, XP002059630.

C.J. Shishoo et al.: "Reaction of Nitriles Under Acidic Conditions. Part IV. Synthesis of Some 2–Substituted Quinazolin–4–ones and Thienopyrimidin–4–ones of Biological Interest and Isolation of o–functionalized amidine intermediates," Indian Journal of Chemistry Section B., vol., 28B, No. 12, Dec. 1989, pp. 1039–1047, XP000983872, p. 1039, col. 1, paragraph 1—p. 1040, col. 2, paragraph 1.

C.J. Shishoo et al.. "Reaction of Nitriles Under Acidic Conditions. Part III. A Facile Synthesis of Thienopyrimidin–4(3H)–ones," Journal of Heterocyclic Chemistry, vol. 21, No. 2, Mar. 1984, pp. 375–380, XP000983906, p. 3756, Schemes I–III.

C.J. Shishoo et al., "Studies on the Synthesis of 2–(2–Arylvinyl)thieno'2,3–d!pyrimidines," Journal of Heterocyclic Chemistry, vol. 22, No. 3, May 1985, pp. 825–830, XP000983905, p. 825, Schemes I–II.

*Primary Examiner*—John M. Ford
(74) *Attorney, Agent, or Firm*—Millen, White, Zelano & Branigan, P.C.

(57) ABSTRACT

The invention relates to a process for preparing compounds of the formula I

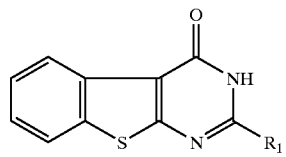

I

In this process a 2-aminobenzothiophene-3-carboxylic ester of the formula II

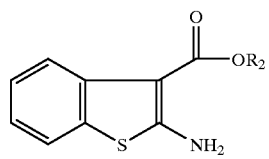

II is reacted with a nitrile of the formula III

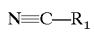

III in solution or suspension in a solvent in the presence of an acid.

21 Claims, No Drawings

METHOD FOR PRODUCING THIENOPYRIMIDINES

The invention relates to a process for preparing compounds of the formula I

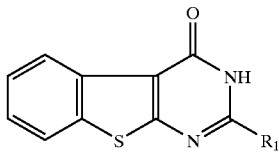

where $R^1$ is a linear or branched alkyl radical having from 1 to 10 carbon atoms, in which one or two $CH_2$ groups may be replaced by —CH=CH groups or a cycloalkyl radical or cycloalkylalkylene radical having from 5 to 12 carbon atoms or a phenyl radical or phenylmethyl radical and said radicals are monosubstituted by —COOH, —COOA, —CONH$_2$, —CONHA, —CON(A)$_2$ or —CN where A is an alkyl group having from 1 to 6 carbon atoms.

Compounds of the formula I constitute an effective starting point for the synthesis of medicaments, since the presence of the carbonyl group of pyrimidine makes it possible to attach various radicals, thereby paving the way for the synthesis of novel medicinal substances whose properties may be modified by varying the group to be attached.

Medicinal substances containing the heterocyclic system of compounds of the formula I are described, for example, in DE-198 190 23 A1. These compounds and the salts thereof show good tolerability and possess very valuable pharmacological properties. They show in particular a specific inhibition of cGMP phosphodiesterase (PDE V). Therefore the compounds are suitable for the treatment of diseases of the cardiovascular system, in particular heart failure, and for the treatment and/or therapy of impaired potency (erectile dysfunction).

For broad application of these medicinal substances it is necessary to be able to provide sufficient amounts of suitable starting compounds. The medicinal substances should be obtained in great purity because of the rigorous demands on their purity. Furthermore the reaction should result in a high yield in order to keep costs down and to avoid waste disposal problems.

Houben-Weyl, E9b/2, page 29 to 30 describes the preparation of 2-substituted quinazolin-4(3H)-ones. In this process anthranilic acid or anthranilic esters are reacted with nitriles.

In J. Heterocyclic Chem. 17, 1497 (1980) K. G. Dave et al. describe a process for preparing condensed pyrimidines. The synthesis of benzothieno[3,2-d]pyrimidines and of substituted 4-ethoxy-5,6,7,8-tetrahydrobenzo[b]thieno[2,3-d] pyrimidines is described inter alia.

The object of the invention is to provide a process for preparing compounds of the formula I which is simple to carry out and provides the compounds of the formula I in good yields and high purity.

This object is achieved by a process for preparing compounds of the formula I wherein a 2-aminobenzothiophene-3-carboxylic ester of the formula II

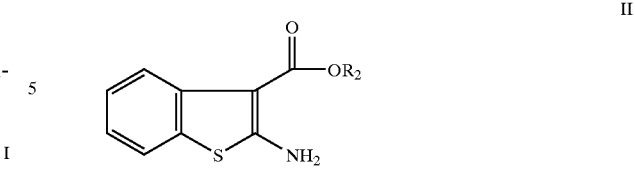

where $R^2$ is a linear or branched alkyl group having from 1 to 6 carbon atoms, in particular methyl, and a nitrile of the formula III

where $R^1$ has the above meaning in solution or suspension in a solvent is reacted in the presence of an acid.

Preferably methyl, ethyl or propyl, furthermore preferably isopropyl, butyl, isobutyl, sec-butyl or tert-butyl, but also n-pentyl, neopentyl, isopentyl or hexyl is used as radical $R^2$ of the carboxylic ester of the formula II. For the radical $R^1$ of the nitrile of the formula III linear or branched alkyl radicals having from 1 to 10 carbon atoms may be used, in which one or two $CH_2$ groups may be replaced by —CH=CH— groups. The alkyl radical used is preferably, for example, methyl, ethyl, propyl, isopropyl, butyl, isobutyl, sec-butyl, pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-3-methylpropyl, 1,1,2- or 1,2,2-trimethylpropyl, linear or branched heptyl, octyl, nonyl or decyl. Furthermore $R^1$ may be but-2-enyl or hex-3-enyl.

Cycloalkyl radicals or cycloalkylalkylene radicals having from 5 to 12 carbon atoms which may be used are cyclopentylmethylene, cyclohexylmethylene, cyclohexylethylene, cyclohexylpropylene or cyclohexylbutylene. The cycloalkyl radicals preferably comprise from 5 to 7 carbon atoms. Examples are cyclopentyl, cyclohexyl or cycloheptyl groups. Furthermore $R^1$ may be a phenyl or phenylmethyl radical.

Each of said radicals is mono-substituted by —COOH, —COOA, —CONH$_2$, —CONHA, —CON(A)$_2$ or —CN. A is in this case alkyl having from 1 to 6 carbon atoms. Examples of suitable groups are methyl, ethyl or propyl, and isopropyl, butyl, isobutyl, sec-butyl or tert-butyl, and also n-pentyl, neopentyl, isopentyl or hexyl.

In the process according to the invention the compounds of the formula I are obtained as salts. These precipitate in general from the reaction solution as a crystalline precipitate and may be obtained in sufficient purity by simple filtering off.

The synthesis of the compound of the formula I is in general carried out by initially introducing the carboxylic ester of the formula II and the nitrile of the formula III into a suitable solvent and then adding the acid, for example by passing it into the solution as a gas.

However, it is possible to significantly increase the reaction yield and the purity of the reaction product of the formula I and further to shorten the reaction time if initially an excess of acid is dissolved in the solvent, preferably the solvent is saturated with the acid, and subsequently the 2-aminobenzothiophene-3-carboxylic ester of the formula II and the nitrile of the formula III are added.

An excess of acid is an amount of acid so large that after quantitative reaction of the compounds of the formulae I and II and subsequent precipitation as salt unbound acid still remains in the solution. This amount of acid is to be already present in the reaction mixture at the start of the reaction.

The reaction may proceed such that first a, preferably saturated, solution of the acid in the solvent is prepared and separately therefrom a solution which contains the compounds of the formula I and the formula II. It is possible either for the two solutions then to be introduced simultaneously into a reaction vessel for the reaction or for the acid solution to be initially charged and the solution of the compounds of the formula I and the formula II to be added. It is, however, also possible to initially charge the solution of the compounds of the formula I and the formula II and to add the acid solution. However, in this case the acid solution should be added very rapidly to the solution of the compounds of the formula I and the formula II.

It has proved to be appropriate for the solvent to be selected from the group consisting of ethers, alcohols, esters, water, formamides, amines, carboxylic acids, chlorinated hydrocarbons and mixtures thereof. A particularly suitable solvent is dioxane.

Suitable ethers are, for example, diethyl ether, diisopropyl ether, tetrahydrofuran or dioxane. Suitable alcohols are, for example, methanol, ethanol, isopropanol, n-propanol, n-butanol or tert-butanol. Also suitable are glycol ethers such as ethylene glycol monomethyl ether or ethylene glycol monoethyl ether (methylglycol or ethylglycol), diethylene glycol dimethyl ether (diglyme). Suitable amides are, for example, acetamide, dimethylacetamide, N-methylpyrrolidone or dimethylformamide. A suitable carboxylic acid is, for example, glacial acetic acid. An ester which may be used is, for example, ethyl acetate. Suitable chlorinated hydrocarbons are, for example, trichloroethylene, 1,2-dichloroethane, carbon tetrachloride, chloroform or dichloromethane. It is also possible to employ mixtures of the solvents mentioned.

The acids are suitably selected from the group consisting of Brönsted acids and Lewis acids, in particular hydrochloric acid, hydrobromic acid, sulfuric acid, phosphoric acid, polyphosphoric acid, methanesulfonic acid, trifluoromethanesulfonic acid, trifluoroacetic acid, aluminium trichloride and boron trifluoride. Particularly suitable are gaseous acids, in particular hydrogen chloride.

The reaction is suitably carried out at a temperature of from −10° C. to 100° C., preferably 0° C. to 60° C., in particular 10° C. to 50° C.

In a particularly preferred embodiment of the process according to the invention the addition of acid to the mixture is continued during the reaction. Thus it is possible to achieve nearly quantitative precipitation of the compound of the formula I as salt of the acid.

The compounds of the formula I constitute a valuable starting substance for further syntheses. It is possible to achieve further activation of the compound of the formula I, if in a further step the compound of the formula I is converted into a compound of the formula IV

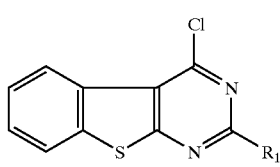

IV by a chlorinating agent. The chlorine may simply be substituted by appropriate nucleophiles.

The chlorinating agent is suitably selected from the group consisting of $SOCl_2$, $POCl_3$, $PCl_5$, $ClCOCOCl$.

The compounds of the formulae II and III are either known or may be prepared by the skilled worker using known synthesis pathways. An example of a synthesis of the compounds of the formulae II and III is described in the following with particularly preferred compounds. For other radicals $R^1$ and $R^2$ the reactions can be carried out analogously.

Synthesis of methyl 2-aminobenzothiophene-3-carboxylate 7 starts from thiosalicylic acid 1. The carboxyl group is reduced by lithium aluminium hydride resulting in the alcohol 2. Afterwards the thiol group is reacted with benzyl chloride to give the thioether 3. Next the hydroxyl group of the compound 3 is reacted with hydrochloric acid to give the chloride 4 which is then reacted with sodium cyanide to give the nitrile 5. This is reacted with dimethyl carbonate to give the compound 6 which is finally cyclized to give the compound 7.

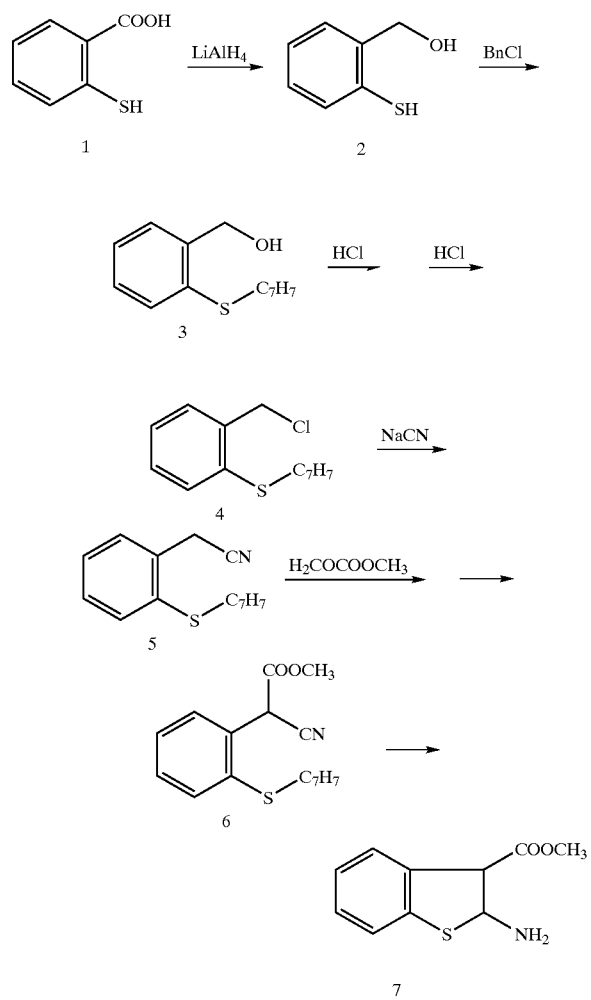

Synthesis of the preferred methyl trans-4-cyanocyclohexanecarboxylate starts from methyl trans-cyclohexane-1,4-dicarboxylate 8 which is first hydrolysed by KOH to give the monomethyl ester 9. This is first converted into the acid chloride by thionyl chloride and then into the acid amide 10 by ammonia. The nitrile 11 is finally obtained from the acid amide 10.

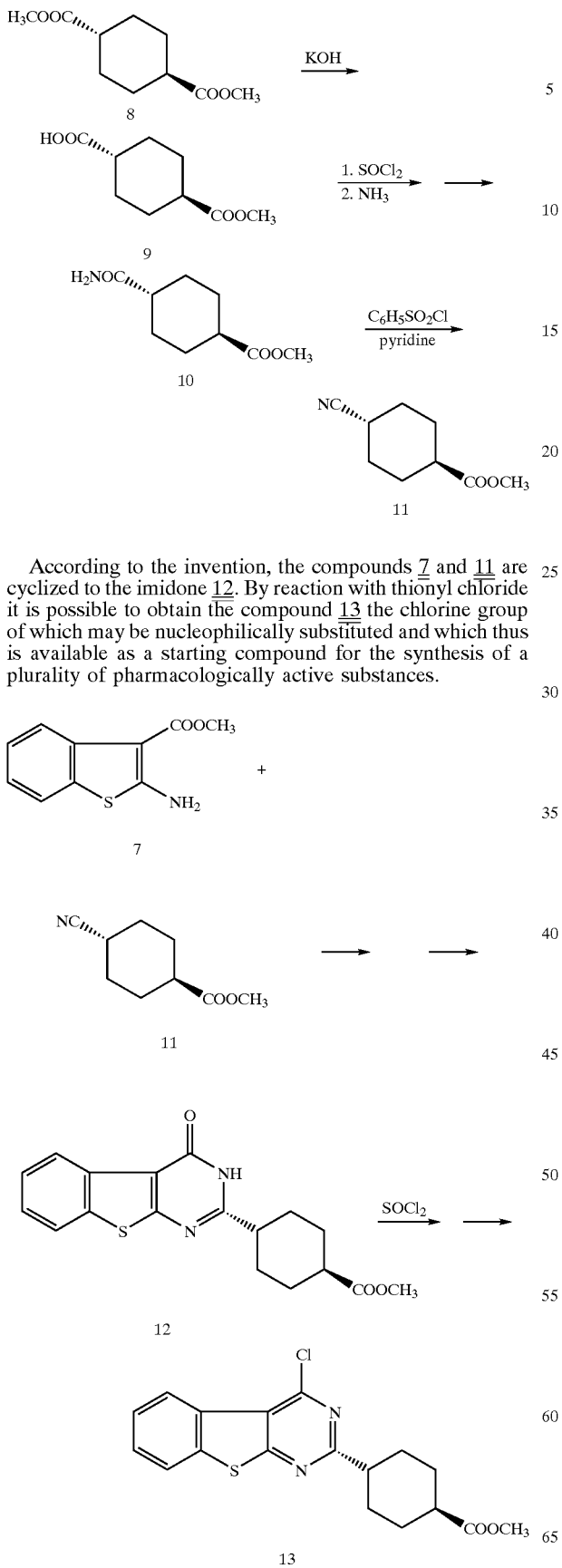

According to the invention, the compounds 7 and 11 are cyclized to the imidone 12. By reaction with thionyl chloride it is possible to obtain the compound 13 the chlorine group of which may be nucleophilically substituted and which thus is available as a starting compound for the synthesis of a plurality of pharmacologically active substances.

In the following, the invention is illustrated by examples.

EXAMPLE 1

Preparation of methyl 4-(benzothieno[2,3-d]3H-4-oxo-pyrimidin-2-yl)cyclohexanecarboxylate 12
(variant A)

9079 g of methyl 2-aminobenzothiophene-3-carboxylate 7 and 8600 g of methyl trans-4-cyanocyclohexanecarboxylate 11 were dissolved in 50 l of 1,4-dioxane. The mixture was heated to 45° C. and HCl gas was passed into the mixture for 15 hours. The reaction was followed by thin layer chromatography (methanol/methylene chloride=1:1). After ten days the precipitate was removed by filtration and dried, yield 79.1%. Analysis by HPLC (acetonitrile/H$_2$O 60:40 (v/v); 0.1% (Vol) trifluoroacetic acid added) revealed a purity of 86%. This corresponds to a yield based on content of 68%.

EXAMPLE 2

Preparation of methyl 4-(benzothieno[2,3-d]3H-4-oxo-pyrimidin-2-yl)cyclohexane-carboxylate 12
(variant B)

50 l of 1,4-dioxane were initially charged into a first feed vessel and the temperature was adjusted to 10° C. 14.8 kg of HCl gas were subsequently passed in over 15.5 h.

50 l of 1,4-dioxane were initially charged into a second reaction vessel and 9079 g of methyl 2-aminobenzothiophene-3-carboxylate 7 and 8600 g of methyl trans-4-cyanocyclohexanecarboxylate 11 were introduced. The reaction mixture was heated to 45° C. and subsequently the HCl-saturated 1,4-dioxane solution was added over 20 min. During the addition a beige precipitate crystallized. A further 6 kg of HCl gas were passed in at an internal temperature of from 34° C. to 45° C. over 4.75 h. The reaction mixture was stirred overnight at 34° C. The next day a further 10 kg of HCl gas were passed in over 8 h and the reaction mixture was stirred overnight. The precipitate was removed and suspended in 60 l of deionized water. The pH was adjusted to pH 9 by adding 12 l of aqueous ammonia (13% by weight). After finishing the addition, stirring was continued for a further 45 min and the crystallized precipitate was filtered off via a suction funnel. The filter residue was washed twice with 12 l of deionized water and the product was subsequently dried under reduced pressure at 50° C.

Yield 10.75 kg of white crystals, m. p. >300° C.

EXAMPLE 3

Preparation of methyl 4-(4-chlorobenzothieno[2,3-d]pyrimidin-2-yl)cyclohexanecarboxylate 13

12.5 l of thionyl chloride were initially charged and cooled with stirring to 25° C. Then 2320 g of 12 were introduced and 1100 ml of dimethylformamide were added dropwise. After stirring overnight the solvent was stripped off under reduced pressure. The crystalline residue was dissolved in dichloromethane and then slowly added to ice/water. The organic phase was removed. The aqueous phase was extracted three times with dichloromethane. The combined organic phases were extracted with water, aqueous sodium hydroxide and again water and then dried over sodium sulfate. After filtration the solvent was distilled off under reduced pressure. The crystalline residue was washed in the cold with diisopropyl ether and subsequently the crystals were removed by filtration. The crystals were dried to constant mass at 50° C.

Yield: 1420 g of yellow crystals
m.p.: 127° C.

What is claimed is:

1. A process for preparing a compound of formula I

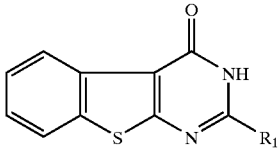

wherein $R_1$ is
  a linear of branched alkyl radical having 1 to 10 carbon atoms, in which one or two $CH_2$ groups are optionally each replaced by a —CH=CH— group,
  a cycloalkyl radical or cycloalkylalkylene radical having 5 to 12 carbon atoms, or
  a phenyl radical or phenylmethyl radical
wherein the radicals are mono substituted with COOH, COOA, $CONH_2$, CONHA, $CON(A)_2$ or CN, wherein A is an alkyl group having from 1 to 6 carbon atoms,
  comprising reacting a 2-aminobenzothiophene-3-carboxylic ester of formula II

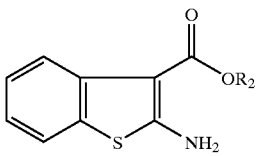

wherein $R_2$ is a linear or branched alkyl group having 1 to 6 carbon atoms, with a nitrile of formula III

     III wherein $R_1$ has the above meaning
  in solution or suspension in a solvent in the presence of an acid,
wherein an excess of the acid is dissolved in the solvent, and subsequently the 2-aminobenzothiophene-3-carboxylic ester of formula II and the nitrile of the formula III are added.

2. A process for preparing a compound of formula I

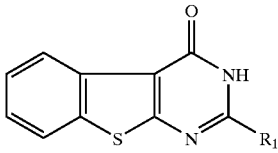

wherein $R_1$ is
  a linear of branched alkyl radical having 1 to 10 carbon atoms, in which one or two $CH_2$ groups are optionally each replaced by a —CH=CH— group,
  a cycloalkyl radical or cycloalkylalkylene radical having 5 to 12 carbon atoms, or
  a phenyl radical or phenylmethyl radical
wherein the radicals are mono substituted with COOH, COOA, $CONH_2$, CONHA, $CON(A)_2$ or CN, wherein A is an alkyl group having from 1 to 6 carbon atoms,
  comprising reacting a 2-aminobenzothiophene-3-carboxylic ester of formula II

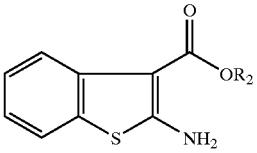

wherein $R_2$ is a linear or branched alkyl group having 1 to 6 carbon atoms,
  with a nitrile of formula III

     III wherein $R_1$ has the above meaning
  in solution or suspension in a solvent in the presence of an acid,
wherein the solvent is selected from the group consisting of ethers, alcohols, esters, water, amides, carboxylic acids, chlorinated hydrocarbons and mixtures thereof.

3. A process for preparing a compound of formula I

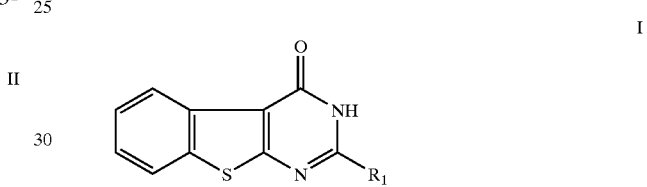

wherein $R_1$ is
  a linear of branched alkyl radical having 1 to 10 carbon atoms, in which one or two $CH_2$ groups are optionally each replaced by a —CH=CH— group,
  a cycloalkyl radical or cycloalkylalkylene radical having 5 to 12 carbon atoms, or
  a phenyl radical or phenylmethyl radical
wherein the radicals are mono substituted with COOH, COOA, $CONH_2$, CONHA, $CON(A)_2$ or CN, wherein A is an alkyl group having from 1 to 6 carbon atoms,
  comprising reacting a 2-aminobenzothiophene-3-carboxylic ester of formula II

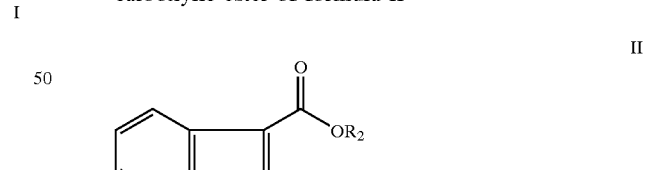

wherein $R_2$ is a linear or branched alkyl group having 1 to 6 carbon atoms,
  with a nitrile of formula III

     III wherein $R_1$ has the above meaning
  in solution or suspension in a solvent in the presence of an acid,
wherein the acid is a Brönsted acid or a Lewis acid.

4. A process for preparing a compound of formula I

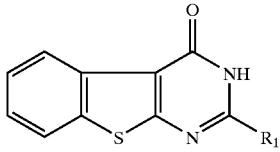

wherein $R_1$ is
- a linear of branched alkyl radical having 1 to 10 carbon atoms, in which one or two $CH_2$ groups are optionally each replaced by a —CH=CH— group,
- a cycloalkyl radical or cycloalkylalkylene radical having 5 to 12 carbon atoms, or
- a phenyl radical or phenylmethyl radical wherein the radicals are mono substituted with COOH, COOA, $CONH_2$, CONHA, $CON(A)_2$ or CN, wherein A is an alkyl group having from 1 to 6 carbon atoms, comprising reacting a 2-aminobenzothiophene-3-carboxylic ester of formula II

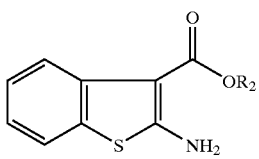

wherein $R_2$ is a linear or branched alkyl group having 1 to 6 carbon atoms, with a nitrile of formula III

    III wherein $R_1$ has the above meaning in solution or suspension in a solvent in the presence of an acid, wherein the reaction is carried out at a temperature of 10° C. to 100° C.

5. A process for preparing a compound of formula I

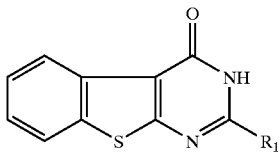

wherein $R_1$ is
- a linear of branched alkyl radical having 1 to 10 carbon atoms, in which one or two $CH_2$ groups are optionally each replaced by a —CH=CH— group,
- a cycloalkyl radical or cycloalkylalkylene radical having 5 to 12 carbon atoms, or
- a phenyl radical or phenylmethyl radical wherein the radicals are mono substituted with COON, COOA, $CONH_2$, CONHA, $CON(A)_2$ or CN, wherein A is an alkyl group having from 1 to 6 carbon atoms, comprising reacting a 2-aminobenzothiophene-3-carboxylic ester of formula II

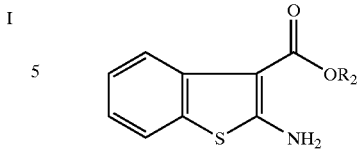

wherein $R_2$ is a linear of branched alkyl group having 1 to 6 carbon atoms, with a nitrile of formula III

    III wherein $R_1$ has the above meaning in solution or suspension in a solvent in the presence of an acid, wherein addition of the acid is continued during the reaction to the solution or suspension.

6. A process for preparing a compound of formula IV

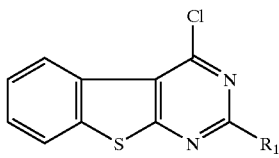

wherein $R_1$ is
- a linear of branched alkyl radical having 1 to 10 carbon atoms, in which one or two $CH_2$ groups are optionally each replaced by a —CH=CH— group,
- a cycloalkyl radical or cycloalkylalkylene radical having 5 to 12 carbon atoms, or
- a phenyl radical or phenylmethyl radical wherein the radicals are mono substituted with COOH, COOA, $CONH_2$, CONHA, $CON(A)_2$ or CN, wherein A is an alkyl group having from 1 to 6 carbon atoms, comprising reacting a 2-aminobenzothiophene-3-carboxylic ester of formula II

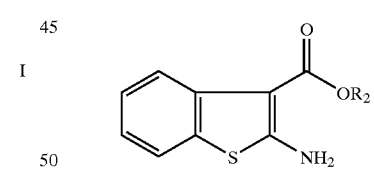

wherein $R_2$ is a linear or branched alkyl group having 1 to 6 carbon atoms, with a nitrile of formula III

    III wherein $R_1$ has the above meaning in solution or suspension in a solvent in the presence of an acid, and reacting the resultant product with $SOCl_2$, $POCl_3$, $PCl_5$, or ClCOCOCl.

7. A process for preparing a compound of formula I according to claim 1, wherein $R_2$ is methyl.

8. A process or preparing a compound of formula I according to claim 1, wherein the solvent is sat rated with the acid.

9. A process or preparing a compound of formula I according to claim 2, wherein wherein the solvent is selected from the group consisting of ethers, alcohols, water, amides, carboxylic acids, chlorinated hydrocarbons and mixtures thereof.

10. A process for preparing a compound of formula I according to claim 3, wherein wherein the acid is hydrochloric acid, hydrobromic acid, sulfuric acid, phosphoric acid, polyphosphoric acid, methanesulfonic acid, trifluoromethanesulfonic acid, trifluoroacetic acid, aluminium trichloride or boron trifluoride.

11. A process for preparing a compound of formula I according to claim 4, wherein the reaction is carried out at a temperature of 0° C. to 60° C.

12. A process for preparing a compound of formula I according to claim 4, wherein the reaction is carried out at a temperature of 10° C. to 50° C.

13. A process for preparing a compound of formula I according to claim 1, wherein $R_1$ is a cyclohexyl radical substituted COOA.

14. A process for preparing a compound of formula I according to claim 2, wherein $R_1$ is a cyclohexyl radical substituted COOA.

15. A process for preparing a compound of formula I according to claim 3, wherein $R_1$ is a cyclohexyl radical substituted COOA.

16. A process for preparing a compound of formula I according to claim 4, wherein $R_1$ is a cyclohexyl radical substituted COOA.

17. A process for preparing a compound of formula I according to claim 5, wherein $R_1$ is a cyclohexyl radical substituted COOA.

18. A process for preparing a compound of formula I according to claim 6, wherein $R_1$ is a cyclohexyl radical substituted COOA.

19. A process for preparing a compound of formula I, A process for preparing a compound of formula I

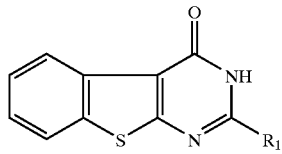

I wherein $R_1$ is a linear of branched alkyl radical having 1 to 10 carbon atoms, in which one or two $CH_2$ groups are optionally each replaced by a —CH=CH— group, a cycloalkyl radical or cycloalkylalkylene radical having 5 to 12 carbon atoms, or a phenyl radical or phenylmethyl radical wherein the radicals are mono substituted with COOH, COOA, $CONH_2$, CONHA, $CON(A)_2$ or CN, wherein A is an alkyl group having from 1 to 6 carbon atoms, comprising reacting a 2-aminobenzothiophene-3-carboxylic ester of formula II

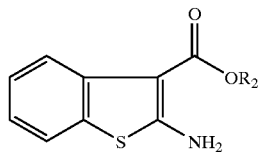

II wherein $R_2$ is a linear or branched alkyl group having 1 to 6 carbon atoms, with a nitrile of formula III

  III wherein $R_1$ has the above meaning in solution or suspension in a solvent in the presence of an acid, wherein the 2-aminobenzothiophene-3-carboxylic ester of formula II and the nitrile of the formula III are dissolved in the solvent and subsequently the acid is added.

20. A process for preparing a compound of formula I according to claim 19, wherein $R_1$ is a cyclohexyl radical substituted COOA.

21. A process for preparing a compound of formula I according to claim 2, wherein the solvent is dioxane.

* * * * *

UNITED STATES PATENT AND TRADEMARK OFFICE
CERTIFICATE OF CORRECTION

PATENT NO. : 6,689,885 B2
DATED : February 10, 2004
INVENTOR(S) : Juraszyk et al.

It is certified that error appears in the above-identified patent and that said Letters Patent is hereby corrected as shown below:

<u>Column 9,</u>
Line 62, reads "COON," should read -- COOH --

Signed and Sealed this

Seventeenth Day of August, 2004

JON W. DUDAS
*Acting Director of the United States Patent and Trademark Office*